United States Patent [19]

Carr et al.

[11] Patent Number: 5,430,190
[45] Date of Patent: Jul. 4, 1995

[54] PROPOXYLATION AND REDUCTIVE ALKYLATION OF DIETHYLENETRIAMINE

[75] Inventors: Richard V. C. Carr, Allentown; Craig R. Williams, Macungie, both of Pa.

[73] Assignee: Air Products and Chemicals, Inc., Allentown, Pa.

[21] Appl. No.: 259,721

[22] Filed: Jun. 14, 1994

[51] Int. Cl.$^6$ .................................. C07C 209/26
[52] U.S. Cl. .......................... 564/477; 564/475; 564/503; 564/512
[58] Field of Search ............... 564/503, 512, 475, 477

[56] References Cited

U.S. PATENT DOCUMENTS

| | | | |
|---|---|---|---|
| 4,026,840 | 5/1977 | Bechara et al. | 521/118 |
| 4,338,408 | 7/1982 | Zimmerman et al. | 564/475 |
| 4,433,170 | 2/1984 | Zimmerman et al. | 564/475 |

FOREIGN PATENT DOCUMENTS 59-199655  11/1984  Japan .

*Primary Examiner*—Glennon H. Hollrah
*Assistant Examiner*—Scott C. Rand
*Attorney, Agent, or Firm*—Michael Leach; William F. Marsh

[57] ABSTRACT

A one-pot reaction process for the coproduction of two polyurethane catalysts which comprises reacting excess diethylenetriamine (DETA) in a reaction vessel with propylene oxide in the presence of a hydrogenation catalyst under conditions and for a period of time to essentially completely react the propylene oxide to give a mixture of DETA and N-2-hydroxypropyldiethylenetriamine (HPDETA), adding formaldehyde and hydrogen to the reaction vessel, reacting the DETA and HPDETA with the formaldehyde and hydrogen under conditions to effect permethylation of the DETA and HPDETA to afford N,N,N',N',N''-pentamethyldiethylenetriamine (PMDETA), a polyurethane catalyst, and N-2-hydroxypropyl-N,N',N',N''-tetramethyldiethylenetriamine (HPTMDETA) a nonfugitive polyurethane catalyst.

18 Claims, No Drawings

PROPOXYLATION AND REDUCTIVE ALKYLATION OF DIETHYLENETRIAMINE

FIELD OF THE INVENTION

The present invention pertains to a method for making hydroxy-containing polyurethane amine catalysts.

BACKGROUND OF THE INVENTION

Commercial manufacture of nonfugitive polyurethane amine catalysts, i.e., hydroxy-containing amine catalysts, is becoming more important as environmental regulations become more stringent. A common design approach to nonfugitive catalysts is to prepare hydroxyl-containing analogs of existing tertiary amine catalysts. For example, diethylenetriamine (DETA) is reductively alkylated with formaldehyde to give N,N,N',N',N''-pentamethyldiethylenetriamine (PMDETA), a commercial tertiary amine blowing catalyst. A nonfugitive analog of PMDETA is N-2-hydroxypropyl-N,N',N',N''-tetramethyldiethylenetriamine (HPTMDETA) prepared by first reacting propylene oxide with DETA (Equation 1), followed by reductive alkylation with formaldehyde (Equation 2).

polyalkylene polyamine is reacted with an alkylene oxide in the presence of a hydrogenation catalyst in a reactor under conditions to achieve essentially complete reaction of the alkylene oxide to afford a mixture of hydroxyalkylated polyalkylene polyamine and polyalkylene polyamine. Hydrogen is then charged to the reactor followed by formaldehyde addition over a period of time, under conditions to effect permethylation. The resulting permethylated polyalkylene polyamine and hydroxyalkylated permethylated polyalkylene polyamine are separated.

In the preferred embodiment, the present invention provides a process for the coproduction of PMDETA and HPTMDETA in a one-pot operation. DETA is reacted with propylene oxide in the presence of a hydrogenation catalyst. After essentially complete reaction of the propylene oxide, hydrogen is charged to the reactor and formaldehyde is charged over a period of time and reacted. The resulting PMDETA and HPTMDETA are separated, preferably by vacuum distillation.

By allowing the coproduction of PMDETA and HPTMDETA, the intermediate DETA distillation and recycle operation is avoided. In addition, coproduction Equation 1

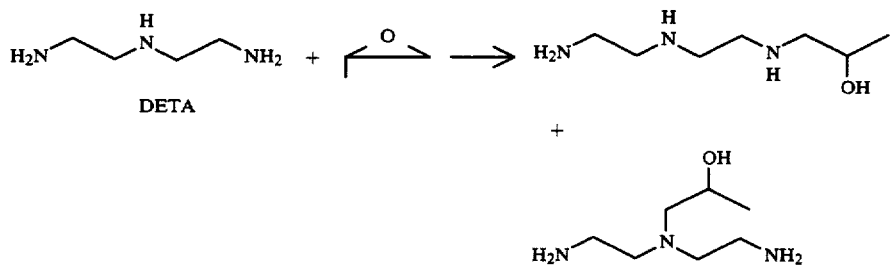

Equation 2

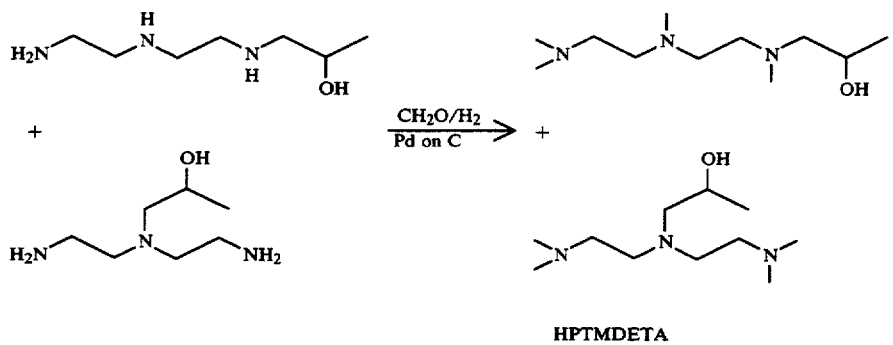

HPTMDETA

The principal hurdle to overcome in this HPTMDETA process is the fact that large excesses (100–200%) of DETA must be employed to achieve high (80–90%) yields of monopropoxylated product. The excess unreacted DETA may, of course, be recycled, but this requires an intermediate distillation and, as such, precludes conducting the two reactions in a simplified one-pot process.

SUMMARY OF THE INVENTION

In its broadest sense, the present invention provides a one-pot process for the coproduction of a permethylated polyalkylene polyamine and a hydroxyalkylated permethylated polyalkylene polyamine. The also allows for conducting the alkoxylation and the reductive alkylation sequentially in the same reaction vessel without the necessity of the intermediate discharging and charging of vessels inherent in a discrete two-stage process.

The one-pot process is only feasible if the hydrogenation catalyst, present in the polyalkylene polyamine prior to the alkoxylation, has no adverse effect on the alkoxylation. Likewise, the alkoxylation step must not have an adverse effect on the selectivity or activity of the hydrogenation catalyst.

DETAILED DESCRIPTION OF THE INVENTION

In the process reaction according to the invention, any linear or branched polyalkylene polyamine can be used, for example, polyethylene and polypropylene polyamines such as ethylenediamine, propylenediamine, dipropylenetriamine, triethylenetetramine, tetraethylenepentamine, the preferred diethylenetriamine, and the like.

The polyalkylene polyamine can be reacted with a $C_2$–$C_8$ alkylene oxide, such as ethylene oxide, butylene oxide, styrene oxide and the preferred propylene oxide. The alkoxylation reaction may be conducted at temperatures ranging from 40°–120° C., preferably 60°–90° C., at pressures ranging from 1 to 10 bar and for a period of time sufficient to effect the required alkoxylation. In order to obtain the coproduction of a permethylated polyalkylene polyamine and a hydroxyalkylated permethylated polyalkylene polyamine, the polyalkylene polyamine should be reacted with an amount of alkylene oxide insufficient to alkoxylate all of the polyalkylene polyamine. The relative amounts of the two co-products desired will define the amount of alkylene oxide used, although an excess of polyamine, on a molar basis, will normally be used. Thus, the materials may be reacted in an alkylene oxide:polyalkylene polyamine mole ratio of 0.1 to 1, preferably 0.25 to 0.75. Even at a 1:1 mole ratio there will be unreacted polyalkylene polyamine because of the dialkoxylation that occurs.

The alkoxylation reaction of the polyalkylene polyamine takes place in the reactor in the presence of a hydrogenation catalyst. Suitable catalysts include platinum, nickel, rhodium and preferably palladium. The reductive methylation step may be conducted at temperatures ranging from 60°–140° C., preferably 80°–120° C., hydrogen pressures ranging from 3.5 to 138 bar (50–2000 psig), preferably 6.9 to 55 bar (100–800 psig), and periods of time sufficient to effect the reductive methylation.

The reductive methylation is accomplished using formaldehyde. Formaldehyde is added to the reaction vessel over a period of 4–15 hr, preferably 6–12 hr. The amount of formaldehyde added is at least that stoichiometric amount necessary to effect the degree of methylation desired, i.e., one mole of formaldehyde for each N-methyl group to be introduced onto the nitrogen atoms of the molecule. In addition to aqueous formaldehyde solutions, other sources of formaldehyde such as methanolic or butanolic formaldehyde solutions may be used.

Thus, according to the invention, reaction of ethylenediamine (EDA) with propylene oxide, followed by reaction of the hydroxypropylated EDA with formaldehyde in the presence of hydrogen, would yield a blend of tetramethylethylenediamine and N-hydroxypropyltrimethylethylenediamine.

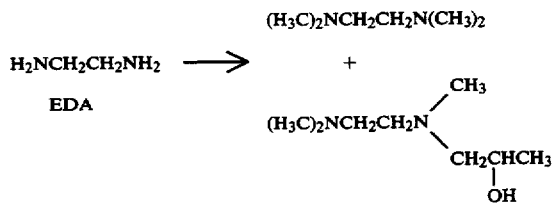

Using triethylenetetramine (TETA), the inventive process yields hexamethyltriethylenetetramine and N-hydroxypropylpentamethyltriethylenetetramine.

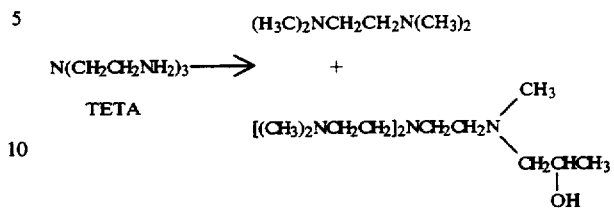

EXAMPLE 1

Preparation and Separation of PMDETA/HPTMDETA

Into a 7.57 liter (2 gal) stainless steel autoclave were charged 1158 g of DETA and 60.1 g of 5 wt % palladium on carbon (50 wt % water wet). The reaction vessel was sealed and purged with nitrogen. The contents of the reaction vessel were then heated to 70° C. and 218.3 g (0.33 mole equivalents) of propylene oxide were metered in at a rate of 2 g/min. Following the propylene oxide addition, the reactor contents were heated to 90° C. and hydrogen was admitted to the reactor until a pressure of 55 bar (800 psig) was achieved, 37 wt % aqueous formaldehyde was then pumped into the reactor at a rate of 10 g/min until a total of 4497 g had been added. The hydrogen pressure was maintained at 55 bar (800 psig) throughout the reaction by the admission of hydrogen from a 3.79 liter (one gal) ballast on demand by a dome regulator. Following the formaldehyde addition, the hydrogen uptake ceased immediately. The reactor contents were analyzed by GC/FID to be 64.3 area % PMDETA, 33.6 area % HPTMDETA, 3.5 area % dihydroxypropyltrimethyldiethylenetriamine, and 0.8% miscellaneous.

The contents of the reactor were partially evaporated at 50 torr to remove methanol and water and then distilled through a packed distillation column with 36 theoretical plates. 1302 g of PMDETA of >994 purity was recovered at 68°–75° C. at 3.2 torr. A 55 g transition cut was then taken at 76°–119° C. at the same pressure. Finally, 671 g of HPTMDETA of 98.5% purity was recovered at 115°–118° C. at 2.6 torr. The distillation residue (111 g) contained 354 of unrecovered HPTMDETA, the remainder being dihydroxypropyltrimethyldiethylenetriamine and miscellaneous heavy materials.

STATEMENT OF INDUSTRIAL APPLICATION

The present inventive process provides a process for the coproduction of PMDETA and HPTMDETA polyurethane catalysts.

We claim:

1. A one-pot reaction process which comprises reacting a polyalkylene polyamine with an alkylene oxide in a reaction vessel in the presence of a hydrogenation catalyst in an alkylene oxide:polyalkylene polyamine mole ratio and under reaction conditions to produce a mixture of hydroxyalkylated polyalkylene polyamine and polyalkylene polyamine, adding sufficient hydrogen and formaldehyde to the reaction vessel to permethylate the mixture and reacting the mixture with the formaldehyde and hydrogen under reductive methylation conditions to produce hydroxyalkylated permethylpolyalkylene polyamine and permethylated polyalkylene polyamine.

2. The process of claim 1 in which the alkylene oxide:polyalkylene polyamine molar ratio is 0.1:1 to 1:1.

3. The process of claim 1 in which the polyalkylene polyamine is ethylenediamine, propylenediamine, diethylenetriamine, dipropylenetriamine, triethylenetetramine and tetraethylenepentamine.

4. The process of claim 1 in which the alkylene oxide is a $C_2$–$C_8$ alkylene oxide.

5. The process of claim 1 in which the alkoxylation reaction is performed at 40° to 120° C. and 1 to 10 bar.

6. The process of claim 1 in which the reductive methylation is performed at 60° to 140° C. and a hydrogen pressure of 3.5 to 138 bar.

7. A one-pot reaction process for the coproduction of N,N,N',N',N''-pentamethyldiethylenetriamine (PMDETA) and N-2-hydroxyalkyl-N,N',N',N''-tetramethyldiethylenetriamine which comprises reacting diethylenetriamine in a reaction vessel with an alkylene oxide which is ethylene oxide, propylene oxide, butylene oxide or styrene oxide in the presence of a hydrogenation catalyst under reaction conditions and in an alkylene oxide:diethylenetriamine mole ratio to produce a mixture of hydroxyalkylated diethylenetriamine and diethylenetriamine, adding to the reaction vessel sufficient hydrogen and formaldehyde to permethylate the mixture and reacting the hydrogen and formaldehyde with the mixture under reductive methylation conditions to produce hydroxyalkylated tetramethyldiethylenetriamine and pentamethyldiethylenetriamine.

8. The process of claim 7 in which the alkoxylation reaction is performed at 40° to 120° C. and 1 to 10 bar.

9. The process of claim 8 in which the alkoxylation reaction is performed at 60° to 90° C.

10. The process of claim 8 in which the reductive methylation is performed at 60° to 140° C. and a hydrogen pressure of 3.5 to 138 bar.

11. The process of claim 10 in which the reductive methylation is performed at 80° to 120° C. and a hydrogen pressure of 6.9 to 55 bar.

12. A one-pot reaction process for the coproduction of N,N,N',N',N''-pentamethyldiethylenetriamine and N-2-hydroxypropyl-N,N',N',N''-tetramethyldiethylenetriamine which comprises reacting diethylenetriamine in a reaction vessel with propylene oxide in a propylene oxide:diethylenetriamine mole ratio of 0.25 to 0.75 in the presence of a hydrogenation catalyst which is platinum, nickel, rhodium or palladium at 40° to 120° C. and 1 to 10 bar pressure to yield a mixture comprising hydroxypropylated diethylenetriamine and diethylenetriamine, adding sufficient hydrogen and formaldehyde to the reaction vessel to permethylate the mixture and reacting the mixture with the formaldehyde and hydrogen under hydrogen pressures ranging from 3.5 to 138 bar and 60° to 140° C. to produce N-2-hydroxypropyl-N,N',N',N''-tetramethyldiethylenetriamine and N,N,N',N',N''-pentamethyldiethylenetriamine.

13. The process of claim 1 in which the hydroxyalkylated permethylpolyalkylene polyamine and the permethylated polyalkylene polyamine are separated.

14. The process of claim 13 in which the separation is effected by vacuum distillation.

15. The process of claim 7 in which the hydroxyalkylated tetramethyldiethylenetriamine and the pentamethyldiethylenetriamine are separated.

16. The process of claim 15 in which the separation is effected by vacuum distillation.

17. The process of claim 12 in which the N-2-hydroxypropyl-N,N',N',N''-tetramethyldiethylenetriamine and the N,N,N',N',N''-pentamethyldiethylenetriamine are separated.

18. The method of claim 17 in which the separation is effected by vacuum distillation.

* * * * *